United States Patent
Takács et al.

(10) Patent No.: US 10,487,051 B2
(45) Date of Patent: Nov. 26, 2019

(54) PREPARATION OF LATANOPROSTENE BUNOD OF DESIRED, PRE-DEFINED QUALITY BY GRAVITY CHROMATOGRAPHY

(71) Applicant: CHINOIN GYÓGYSZER ÉS VEGYÉSZETI TERMÉKEK GYÁRA ZRT., Budapest (HU)

(72) Inventors: László Takács, Budapest (HU); Ibolya Fekete, Budapest (HU); Péter Buzder-Lantos, Budapest (HU); István Lászlófi, Budapest (HU); Irén Hortobágyi, Budapest (HU); Gábor Havasi, Budapest (HU); Zsuzsanna Kardos, Budapest (HU)

(73) Assignee: CHINOIN GYÓGYSZER ÉS VEGYÉSZETI TERMÉKEK GYÁRA ZRT., Budapest (HU)

( * ) Notice: Subject to any disclaimer, the term of this patent is extended or adjusted under 35 U.S.C. 154(b) by 0 days.

(21) Appl. No.: 15/781,361

(22) PCT Filed: Nov. 11, 2016

(86) PCT No.: PCT/HU2016/000071
§ 371 (c)(1),
(2) Date: Jun. 4, 2018

(87) PCT Pub. No.: WO2017/093771
PCT Pub. Date: Jun. 8, 2017

(65) Prior Publication Data
US 2019/0002405 A1    Jan. 3, 2019

(30) Foreign Application Priority Data
Dec. 4, 2015 (HU) .................................... 1500594

(51) Int. Cl.
*C07C 405/00*    (2006.01)
*B01D 15/38*    (2006.01)

(52) U.S. Cl.
CPC ...... *C07C 405/0041* (2013.01); *C07C 405/00* (2013.01); *B01D 15/38* (2013.01); *C07B 2200/13* (2013.01); *C07C 2601/08* (2017.05)

(58) Field of Classification Search
CPC ............ C07C 405/0041; C07C 405/00; C07C 2601/08; C07B 2200/13; B01D 15/38
See application file for complete search history.

(56) References Cited

FOREIGN PATENT DOCUMENTS

| WO | WO 2005/068421 A1 | 7/2005 |
| WO | WO2005068421 | * 7/2005 |

OTHER PUBLICATIONS

Miller (Tips and Tricks for the Lab: Column Packing, pp. 1-6, Published 2012) (Year: 2012).*
Sorbent Technologies (pp. 1-3, Published 2011) (Year: 2011).*
EOCP (Effective Organic Compound Purification pp. 1-162, Published Sep. 2015 (Year: 2015).*
International Search Report (PCT/ISA/210) issued in PCT/HU2016/000071, dated Feb. 23, 2017.
Written Opinion (PCT/ISA/237) issued in PCT/HU2016/000071, dated Feb. 23, 2017.

* cited by examiner

*Primary Examiner* — Yevgeny Valenrod
*Assistant Examiner* — Blaine G Doletski
(74) *Attorney, Agent, or Firm* — Birch, Stewart, Kolasch & Birch, LLP

(57) ABSTRACT

The subject of the invention is a process for the preparation of Latanoprostene bunod of formula (I) with a purity higher than 95% where chromatography is used applying normal phase gravity silica gel column chromatography where the used silica gel is irregular silica gel or spherical silica gel an as eluent and eluent mixture consisting of an apolar and a polar solvent is used and if desired, contamination of the purified compound of formula I arising from the solvents are removed by silica gel filtration chromatography.

19 Claims, No Drawings

PREPARATION OF LATANOPROSTENE BUNOD OF DESIRED, PRE-DEFINED QUALITY BY GRAVITY CHROMATOGRAPHY

This invention relates to the preparation of Latanoprostene bunod of formula (I) with a purity higher than 95%, within that, preparation of novel high-purity (>99.2%) Latanoprostene bunod.

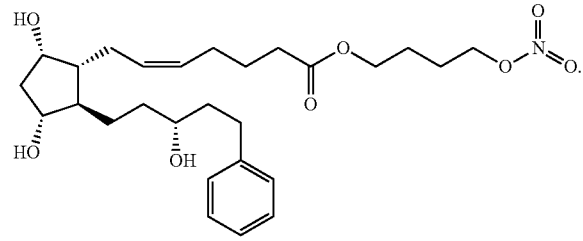

I

Glaucoma is the damage of the optic nerve due to increased eye-pressure which causes sight damage or, if not treated, irreversible blindness. The prevalence of the illness is high and increases with the age. According to world-wide estimations about 60.5 million people were affected by primary open-angle glaucoma or by primary angle-closure glaucoma in 2013. The number of people suffering in glaucoma will increase significantly with the growing average age. (*Ophtalmology*, 2014, 121, 2081-2090).

Glaucoma may be treated by lowering the aqueous humor production (by beta-receptor blockers, alfa-2 receptor agonists, local carboanhydraze blockers) or by increasing the uveoscleral outflow with eye-drops containing prostaglandin active ingredient.

Latanoprost was the first prostaglandin derivative used in the treatment of glaucoma (Stjernschantz J, Resul B. Phenyl substituted prostaglandin analogs for glaucoma treatment *Drugs Future*. 1992; 17, 691-704) which was followed by further PGF2 alpha derivatives (Travoprost, Bimatoprost, Tafluprost, Unoprostone), (Az Egészségügyi Minisztérium szakmai protokollja: A glaukóma kezeléséről/Protocol of the Ministry of Health of Hungary: About the treatment of glaucoma/; Süveges, Ildikó: Szemészet, Medicina Könyvkiadó, 2010: A glaukóma típusai és kezelésük/Suveges, Ildiko, in book Ophtalmology, Medicina Publisher, 2010: Types of glaucoma and their treatment/, http://www.tankonyvtar.hu/hu/tartalom/tamop425/2011_0001_524_szemeszet/ch10s04.html; Lee, David A., Higginbotham, Eve J.: Glaucoma and its treatment: A review, *Am. J. Health_Syst Pharm.*, 2005, 62, 691-699, date of download: 2015 Oct. 15.).

Conventional regulation of the eye-pressure however, does not proceed in the pathway targeted by the antiglaucoma agents, but by regulation of the aqueous outflow through the trabecular meshwork and Schlemm's canal. Under physiological conditions, conventionally, the important cellular signalling molecule, the endogenous nitrogen monoxide also takes part in the process of eye-pressure regulation. (Recent review: Megan E. Cavet, Jason L. Vittitow, Francesco Impagnatiello, Ennio Ongini and Elena Bastia, Nitric Oxide (NO): An emerging target for the treatment of glaucoma. *Invest. Ophtalmol. Vis. Sci.*, 2014, 55, 5005-5015. http://www.iovs.org/content/55/8/5005.short, date of download: 2015 Oct. 15.

The conventional pathway of eye-pressure regulation (trabecular drain-away of the eye-liquid) and the mechanism of action of the PGF2alpha-type antiglaucoma agents (oveoscleral drain-away of the eye liquid) is combined by the prostaglandin nitrooxi derivatives described in patent specification WO2005068421.

The selected molecule is the Latanoprost acid derivative of formula I

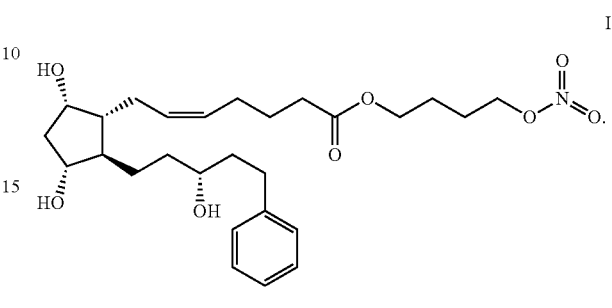

denoted in the specification as NCX-116, INN name: Latanoprostene bunod, which in the body hydrolyses into Latanoprost acid and nitrogen monoxide.

Patent specification WO2005068421 in the Examples part describes the preparation of the molecule of formula I (NCX-116) in mg-scale, but it does not mention the quality of the product and the strategy of purification.

Preparation of Latanoprostene Bunod According to WO2005068421:

Preparation of the Side-Chain:

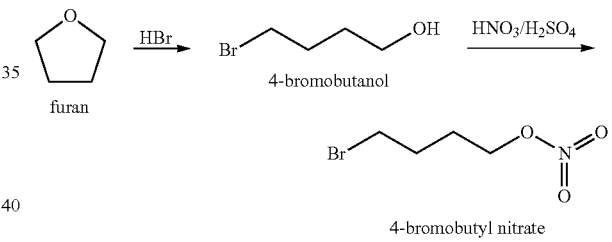

Alkylation of Latanoprost Acid:

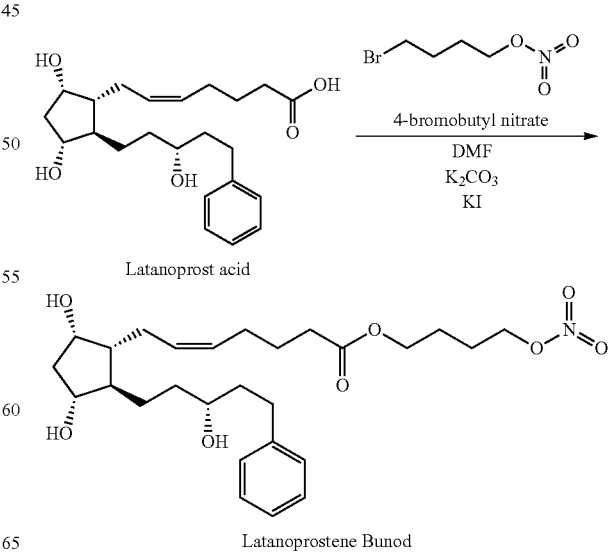

Latanoprost Acid is Obtained by Alkaline Hydrolysis of Latanoprost:

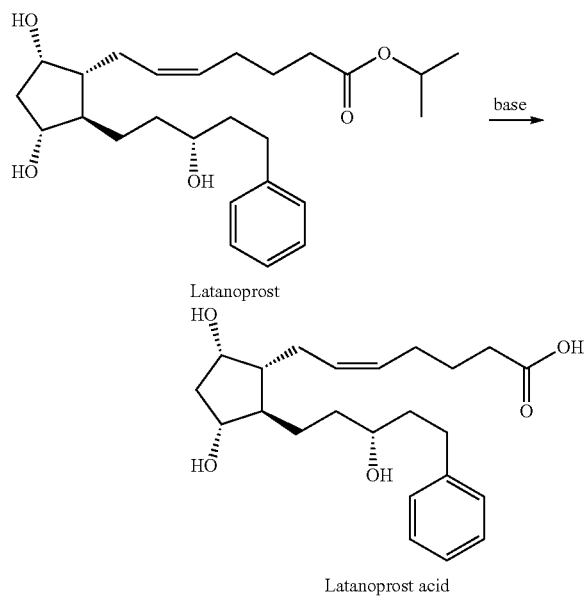

Latanoprost

Latanoprost acid

In the state of the art an active ingredient may be prepared in a desired purity by applying modern chromatography techniques. Increasing the purity of the products, however, significantly increases the production costs. The most effective purification may be achieved by applying high pressure normal and reverse phase preparative liquid chromatography methods. This highly effective purification method however, has numerous disadvantages. The most important factor is the cost, the price of the products purified by this method is significantly increased. High pressure technology requires costly pressure-proof equipment, expensive 5-10 micron particle size silica gel (stationary phase) and expensive filtered and/or distilled high purity solvents (mobile phase).

Further disadvantage is the time requirement. Although the run-time of a separation cycle is short, 1-2 hours, an industrial-scale production may need several tens or hundreds of runs, which considerably elongates the time needed for the separation.

A further task may be to ensure that the already purified, chemically often sensitive product which is in solution in the united main fractions of the runs, does not suffer subsequent decomposition during the process.

Our aim was to elaborate a chromatographic purification process for the crude product of formula I produced by the method described in patent specification WO2005068421 which is economical, robust, scalable and ensures that the resulting purified product does not contain higher level of isomeric and technological impurities than allowed by the limits.

We have found that purifying Latanoprostene bunod crude product by gravity silica gel column chromatography our aim can be fulfilled, since this purification process is cost-saving, robust and easy to scale-up. Applying that process the amount of the isomeric and technological impurities of the product can be decreased to the desired level. A further advantage of the process is that it does not require costly equipment, expensive silica gel and high quantities of purified solvents.

Based on our chromatography experiments we have found that
- Latanoprostene bunod crude product does not contain Latanoprost acid
- impurities x-1 (RRT=0.33) and Latanoprost (RRT=0.81) can be removed on columns packed with either of the two types of silica gels by using any of the investigated eluent mixtures
- for impurity 15S-Latanoprostene bunod a significant decrease may only be achieved by using eluents which contain acetone. Good yield (approx. 74%) can only be achieved on columns packed with the more expensive spherical silica gel
- the amount of the 5,6-trans-Latanoprostene bunod impurity may significantly be decreased (96%) on a column packed with spherical silica gel using hexane:acetone=2:1 eluent mixture, yield: approx. 74%
- impurity x-2 (RRT=1.46) can fully be removed in good yield (>83%) on columns packed with the most economical irregular silica gel, but its amount also decreases significantly (95%) by using hexane:acetone=2:1 eluent mixture on columns packed with spherical silica gel, yield approx. 74%
- all other non-identified, not defined impurities may be removed from the crude product in good yield by using hexane:ethanol eluent mixture on a column packed with irregular silica gel, or using hexane:acetone=2:1 eluent mixture on a column packed with spherical silica gel.

Based on the above results, choosing appropriate silica gel and eluent mixture a Latanoprostene bunod product of desired, pre-defined quality may be produced via the economical gravity column chromatography.

For Latanoprostene bunod no USP requirements have been set. We suppose with good reason that the impurity profile of the Latanoprostene bunod product has to be in line with, or analogously satisfy the USP requirements of the most widely used anti-glaucoma prostaglandin active substance, Latanoprost.

| Latanoprost (USP)* Related impurities (HPLC) | | Latanoprostene bunod Related impurities (HPLC) | |
|---|---|---|---|
| 15S-Latanoprost | ≤0.50% | 15S-Latanoprostene bunod | ≤0.50% |
| 5,6-trans-Latanoprost | ≤3.5% | 5,6-trans-Latanoprostene bunod | ≤3.5% |
| Latanoprost acid | ≤0.10% | Latanoprost | ≤0.50% |
| non-identified impurities individually | ≤0.10% | Latanoprost acid | ≤0.50% |
| non-identified impurities, total | ≤0.30% | non-identified impurities individually | ≤0.10% |
| sum of impurities | ≤5.0% | non-identified impurities, total | ≤0.30% |
| | | sum of impurities | ≤5.0% |

To reach an analogous quality, the highest challenge was to remove impurity RRT=1.46 (x-2) of Latanoprostene bunod.

In that case for the stationary phase we have chosen the most economical and industrially applicable irregular silica gel of pore diameter 60 Angström, particle size 63-200 micron.

For mobile phase bi-component mixtures of apolar and polar solvents of various composition have been chosen.

As the apolar solvent of the bi-component mixture hydrocarbons, halogenated aliphatic hydrocarbons or ether-type solvents have been chosen, such as pentane, hexane, heptane, cyclohexane, dichloromethane or diisopropyl ether.

As for polar solvent we applied an alcohol-, ester- or ketone-type solvent containing straight- or branched-chain alkyl group.

Impurity RRT=1.46 purified well in the investigated solvents, depending on the amount of the silica gel. Also considering the yields, hexane:ethanol gradient mixtures turned out to be the most favourable.

During scale-up using hexane:ethanol eluent mixtures of 6:1, 8:1 compositions, the yield of the purification chromatography was 85-92%.

In order to remove impurities arising from the solvents, the evaporated main fraction of the purification chromatography was filtered on silica gel. This operation is called filtration chromatography.

For stationary phase irregular silica gel of pore diameter 60 Ångström and particle size 63-200 micron has been chosen again.

For mobile phase dichloromethane:ethyl acetate gradient mixtures have been chosen. The yield of the filtration chromatography during scale-up was 91-95%.

The thus elaborated purification process was then scaled-up to 100 g scale.

HPLC purity of the Latanoprostene bunod batches resulting from this purification process met the pre-set requirements.

| Latanoprostene Bunod Related impurities (HPLC) | Requirements | Results | | |
|---|---|---|---|---|
| 15S-Latanoprostene bunod | ≤0.50% | 0.18% | 0.15% | 0.16% |
| 5,6-trans-Latanoprostene bunod | ≤3.5% | 2.6 | 2.4 | 2.3 |
| Latanoprost | ≤0.50% | 0.00 | 0.00 | 0.00 |
| Latanoprost acid | ≤0.50% | 0.00 | 0.00 | 0.00 |
| Non-identified impurities individually | ≤0.10% | | | |
| RRT = 1.46 | | 0.09 | 0.07 | 0.09 |
| Non-identified impurities, total | ≤0.30% | 0.17 | 0.07 | 0.09 |
| Sum of impurities | ≤5.0% | 2.9% | 2.6% | 2.6% |

These experimental data support that gravity chromatography method is also suitable for the preparation of high-purity Latanoprostene bunod.

To achieve a high purity quality not only the level of the non-identified impurities has to be lowered to less than 0.1%, but also the amount of the known, chemically similar and therefore hardly removable isomeric impurities, i.e. 15S-Latanoprostene bunod and 5,6-trans-Latanoprostene bunod have to be decreased significantly.

To prepare high-purity Latanoprostene bunod the crude Latanoprostene bunod was purified on a column packed with 63-200 micron particle size irregular or with the more expensive 50-150 micron particle size spherical silica gel.

For eluent bi-component mixtures of apolar and polar solvents in various compositions were applied. As the apolar solvent of the bi-component mixture hydrocarbons, halogenated aliphatic hydrocarbons or ether-type solvents were applied, such as pentane, hexane, heptane, cyclohexane, and dichloromethane or diisopropyl ether.

As for polar solvent alcohol-, ester- or ketone-type solvents containing straight- or branched-chain alkyl group were applied.

The amount of the 15S-Latanoprostene bunod impurity decreased only in those eluent mixtures which contained a ketone-type solvent.

The amount of the 5,6-trans-Latanoprostene bunod impurity decreased well during chromatography using hexane:acetone, diisopropyl ether:acetone eluent mixtures. The yield of the chromatography was satisfactory however, only if the more expensive spherical silica gel was applied.

Using a column packed with spherical silica gel the hexane:ethanol eluent mixture was also suitable for the separation of the trans isomer.

Regarding the sum of impurities, to prepare high-purity Latanoprostene bunod the crude product has to be chromatographed on a column packed with spherical silica gel and use hexane:acetone=2:1 eluent mixture.

Yield of the purification chromatography is 72-76%. Based on the above experimental results, there is a possibility to prepare high-purity Latanoprostene bunod of the following characteristics:

| Latanoprostene Bunod Related impurities (HPLC) | Requirements |
|---|---|
| 15S-Latanoprostene bunod | ≤0.15% |
| 5,6-trans-Latanoprostene bunod | ≤0.50% |
| Latanoprost | ≤0.10% |
| Latanoprost acid | ≤0.10% |
| Non-identified impurities individually | ≤0.10% |
| Non-identified impurities total | ≤0.30% |
| Sum of impurities | ≤0.80% |

In that case too, the main fraction of the purification chromatography has to be filtered on silica gel in order to remove the organic volatile impurities from the eluents used for purification chromatography. The conditions of the filtration chromatography are the same as given above. The stationary phase is irregular silica gel with pore diameter of 60 Ångström and particle size of 63-200 micron.

As mobile phase gradient mixtures of dichloromethane:ethyl acetate eluents are applied. Yield of the filtration chromatography is 91-95%.

We have worked out a process for the preparation of Latanoprostene bunod active substance of various qualities via purification by gravity chromatography.

The process is suitable to prepare Latanoprostene bunod having impurity levels which are in line with those of the USP quality Latanoprost, by applying the economical irregular Kieselgel 60 silica gel of particle size 63-200 micron.

The process is also suitable for the preparation of high-purity Latanoprostene bunod (sum of impurities ≤0.80%), in that case the more expensive spherical silica gel stationary phase has to be applied.

In accordance with the above, our invention relates to the preparation of Latanoprostene bunod of formula (I) with a purity higher than 95%

I

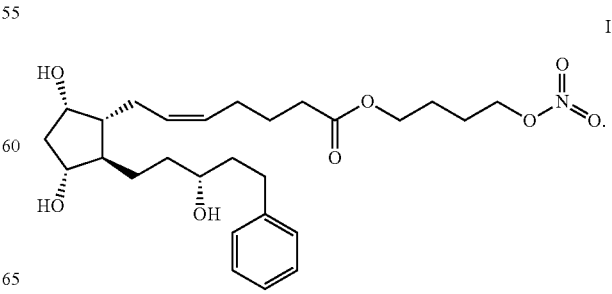

characterized in that the crude Latanoprostene bunod of formula (I) is purified by chromatography, applying normal phase gravity silica gel column chromatography, using as silica gel,
- a.) normal phase, irregular silica gel of particle size 63-200 micron, or
- b.) normal phase spherical silica gel of particle size 50-150 micron, and as eluent, an eluent mixture containing an apolar and a polar solvent, and if desired, impurities arising from the eluents used for purification chromatography of compound of formula are removed by silica gel filtration chromatography.

In the process according to the invention a Latanoprostene bunod product can be produced which meets the following quality requirements:

| Latanoprostene bunod Related impurities (HPLC) | |
|---|---|
| 15S-Latanoprostene bunod | ≤0.50% |
| 5,6-trans-Latanoprostene bunod | ≤3.5% |
| Latanoprost | ≤0.50% |
| Latanoprost acid | ≤0.0% |
| non-identified impurities individually | ≤0.10% |
| non-identified impurities total | ≤0.30% |
| sum of impurities | ≤5.0% |

As apolar solvent, the eluent mixture contains straight- or branched-chain aliphatic, cyclic or aromatic hydrocarbons, halogenated aliphatic hydrocarbons or ether-type solvents, favourably pentane, hexane, heptane, cyclohexane, dichloromethane or diisopropyl ether, preferably hexane.

As polar solvent alcohol-, ester- or ketone-type solvents containing straight- or branched-chain alkyl group may be applied, such as a C1-5 alcohol, preferably ethyl alcohol or isopropyl alcohol.

According to one embodiment of the invention, as silica gel a normal phase irregular silica gel of particle size 63-200 micron is applied, with an eluent containing gradient mixtures of hexane and ethyl alcohol in 6:1-8:1 volume ratios.

According to another embodiment of the invention, for removal of the 5,6-trans-Latanoprostene bunod as polar solvent favourably a ketone-type solvent, preferably acetone is applied. According to a most preferred embodiment, spherical silica gel of 75 micron particle size is used as silica gel and hexane:acetone 2:1 volume ratio mixture as eluent.

In that case the quality of the purified compound of formula I. meets the following quality requirements:

| Latanoprostene Bunod Related impurities (HPLC) | Requirement |
|---|---|
| 15S-Latanoprostene bunod | ≤0.15% |
| 5,6-trans-Latanoprostene bunod | ≤0.50% |
| Latanoprost | ≤0.10% |
| Latanoprost acid | ≤0.10% |
| Non-identified impurities, individually | ≤0.10% |
| Non-identified impurities, total | ≤0.30% |
| Summa of impurities | ≤0.80% |

If desired, impurities arising from the eluents used for purification chromatography of compound of formula are removed by silica gel filtration chromatography. The eluent mixture of the filtration chromatography consists of a polar and an apolar solvent.

As apolar solvent an optionally halogen-substituted straight or branched open-chain aliphatic, or cyclic or aromatic hydrocarbon, while as polar solvent an alcohol-, ether-, ester- or ketone-type solvent containing straight or branched open-chain or cyclic alkyl or cycloalkyl group. In a preferred embodiment the eluent mixture contains dichloromethane and ethyl acetate in 2:1 volume ratio.

Before performing filtration chromatography, the solvents, used as eluents were distilled in a manner that approximately 80% of the solvents were used for chromatography after taking approximately 10% as pre-fraction and leaving approximately 10% as residue.

The quality of the purchased solvents before distillation:

Dichloro methane: Purity by GC≥99.0%

Ethyl acetate: Purity by GC≥99.5%

Advantages of the purification process according to the invention as compared to the preparative and/or flash chromatographic methods:

It is cost-saving and easily realized industrially.

The highly effective purification process is performed by gravity chromatography, which is the most cost-saving chromatography method, since:

it does not require expensive pressure-proof equipment like the medium- and high pressure liquid chromatography systems, the silica gel used as stationary phase in the gravity chromatography is cheaper than the silica gel used in the medium- and high pressure chromatography systems, on the gravity column the purification may be performed in one run, which shortens the production time.

Further details of the invention are demonstrated in the examples without limiting the invention to the examples.

EXAMPLES

1. Example

Purification of Latanoprostene Bunod 4-nitrooxybutyl (Z)-7-[(1R,2R,3R,5S)-3,5-dihydroxy-2-[(3R)-3-hydroxy-5-phenyl-pentyl]cyclopentyl]hept-5-enoate 461.0 g of crude Latanoprostene bunod is dissolved in dichloromethane. The solution is purified by gravity chromatography on a column packed with 100-fold amount (counted for the crude product) of 60 Angstrom pore diameter, 63-200 micron particle size irregular silica gel, using hexane:ethanol=8:1-6:1 eluent mixture. The fractions of appropriate purity are united and evaporated. Yield: 401.1 g (87%). Impurities of the product arising from the eluents used for purification chromatography are removed by filtration chromatography. For dissolution dichloromethane:ethyl acetate mixture is used. The solution is purified by gravity chromatography on a column packed with 10-fold amount (counted for the evaporated product) of 60 Angström pore diameter, 63-200 micron particle size irregular silica gel, using dichloromethane:ethyl acetate=2:1 eluent mixture. The tractions of appropriate purity are united and evaporated. Yield: 364.9 g (91%).

Improvement of the Quality of Latanoprostene Bunod During Purification (HPLC Area %):

| Impurities (HPLC area %) | Crude product | Purification chromatography | Filtration chromatography |
|---|---|---|---|
| RRT = 0.33 | 23.31% | 0.11% | 0.00% |
| RRT = 0.70 (Latanoprost) | 0.08% | 0.00% | 0.00% |
| RRT = 0.81 (Latanoprost acid) | 0.14% | 0.00% | 0.00% |
| 15S-Latanoprostene bunod | 0.11% | 0.08% | 0.08% |
| Latanoprostene bunod | 72.69% | 96.65% | 97.52% |
| 5,6-trans-Latanoprostene bunod | 2.03% | 2.25% | 2.27% |
| RRT = 1.46 | 1.30% | 0.07% | 0.09% |
| Other impurities, total | 0.34% | 0.84% | 0.04% |

2. Example 50.0 g of crude Latanoprostene bunod is dissolved in toluene. Hexane:acetone mixture is added and the solution is purified by gravity chromatography on a column packed with 5000 g of 75 micron particle size, 60 Angström pore diameter YMC spherical silica gel, using hexane:acetone=2:1 mixture eluent. The fractions of appropriate purity are united and evaporated. Yield: 38.0 g (76%).

| Impurities (HPLC area %) | Crude product | Purification chromatography |
|---|---|---|
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.09% |
| Latanoprostene bunod | 72.88% | 99.70% |
| 5,6-trans-Latanoprostene bunod | 2.03% | 0.13% |
| RRT = 1.46 | 1.24% | 0.08% |
| other impurities, total | 0.34% | 0.00% |

3. Example 1.0 g of crude Latanoprostene bunod is dissolved in dichloromethane. Diisopropyl ether:methanol mixture is added and the solution is purified by gravity chromatography on a column packed with 25 g of 63-200 micron particle size, 60 Angström pore diameter irregular silica gel using diisopropyl ether:methanol gradient mixtures as eluent. The fractions of appropriate purity are united and evaporated. Yield: 0.704 g (70%).

| Impurities (HPLC area %) | Crude product | Purification chromatography |
|---|---|---|
| RRT = 0.33 | 23.31% | 1.09% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.16% |
| Latanoprostene bunod | 72.88% | 95.69% |
| 5,6-trans-Latanoprostene bunod | 2.03% | 2.82% |
| RRT = 1.46 | 1.24% | 0.16% |
| other impurities, total | 0.34% | 0.08% |

4. Example 1.0 g of crude Latanoprostene bunod is dissolved in toluene. Hexane:acetone mixture is added and the solution is purified by gravity chromatography on a column packed with 50 g of 63-200 micron particle size, 60 Angström pore diameter irregular silica gel, using hexane:acetone=2:1 mixture eluent. The fractions of appropriate purity are united and evaporated. Yield: 0.55 g (55%).

| Impurities (HPLC area %) | Crude product | Purification chromatography |
|---|---|---|
| RRT = 0.33 | 23.31% | 0.43% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.13% |
| Latanoprostene bunod | 72.88% | 97.42% |
| 5,6-trans-Latanoprostene bunod | 2.03% | 1.06% |
| RRT = 1.46 | 1.24% | 0.86% |
| other impurities, total | 0.34% | 0.10% |

5. Example 1.0 g of crude Latanoprostene bunod is dissolved in toluene. Hexane:acetone mixture is added and the solution is purified by gravity chromatography on a column packed with 100 g of 63-200 micron particle size, 60 Angström pore diameter irregular silica gel, using hexane:acetone=2:1 mixture eluent. The fractions of appropriate purity are united and evaporated. Yield: 0.51 g (51%).

| Impurities (HPLC area %) | Crude product | Purification chromatography |
|---|---|---|
| RRT = 0.33 | 23.31% | 0.17% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.13% |
| Latanoprostene bunod | 72.88% | 98.47% |
| 5,6-trans-Latanoprostene bunod | 2.03% | 0.61% |
| RRT = 1.46 | 1.24% | 0.52% |
| other impurities, total | 0.34% | 0.10% |

6. Example 1.0 of crude Latanoprostene bunod is dissolved in toluene. Hexane:acetone mixture is added and the solution is purified by gravity chromatography on a column packed with 100 g of 75 micron particle size, 60 Angström pore diameter YMC spherical silica gel, using hexane:acetone=2:1 mixture eluent. The fractions of appropriate purity are united and evaporated. Yield: 0.74 g (74%).

| Impurities (HPLC area %) | Crude product | Purification chromatography |
|---|---|---|
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.08% |
| Latanoprostene bunod | 72.88% | 99.71% |
| 5,6-trans-Latanoprostene bunod | 2.03% | 0.12% |
| RRT = 1.46 | 1.24% | 0.09% |
| other impurities, total | 0.34% | 0.00% |

7. Example 1.0 of crude Latanoprostene bunod is dissolved in toluene. Hexane:acetone mixture is added and the solution is purified by gravity chromatography on a column packed with 100 g of 75 micron particle size, 60 Angström pore diameter YMC spherical silica gel, using hexane:acetone=3:2 mixture eluent. The fractions of appropriate purity are united and evaporated. Yield: 0.61 g (61%).

| Impurities (HPLC area %) | Crude product | Purification chromatography |
| --- | --- | --- |
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.12% |
| Latanoprostene bunod | 72.88% | 99.40% |
| 5,6-trans-Latanoprostene bunod | 2.03% | 0.29% |
| RRT = 1.46 | 1.24% | 0.19% |
| other impurities, total | 0.34% | 0.00% |

8. Example 1.0 g of crude Latanoprostene bunod is dissolved in dichloromethane. Diisopropyl ether:acetone mixture is added and the solution is purified by gravity chromatography on a column packed with 100 g of 63-200 micron particle size, 60 Angström pore diameter irregular silica gel, using diisopropyl ether:acetone gradient mixtures as eluent. The fractions of appropriate purity are united and evaporated. Yield: 0.47 g (47%).

| Impurities (HPLC area %) | Crude product | Purification chromatography |
| --- | --- | --- |
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.13% |
| Latanoprostene bunod | 72.88% | 98.57% |
| 5,6-trans-Latanoprostene bunod | 2.03% | 0.70% |
| RRT = 1.46 | 1.24% | 0.49% |
| other impurities, total | 0.34% | 0.11% |

9. Example 1.0 g of crude Latanoprostene bunod is dissolved in dichloromethane. Hexane:isopropanol mixture is added and the solution is purified by gravity chromatography on a column packed with 100 g of 63-200 micron particle size, 60 Angström pore diameter irregular silica gel, using hexane:isopropanol=5:1 mixture eluent. The fractions of appropriate purity are united and evaporated. Yield: 0.56 g (56%).

| Impurities (HPLC area %) | Crude product | Purification chromatography |
| --- | --- | --- |
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.15% |
| Latanoprostene bunod | 72.88% | 96.64% |
| 5,6-trans-Latanoprostene bunod | 2.03% | 2.73% |
| RRT = 1.46 | 1.24% | 0.40% |
| other impurities, total | 0.34% | 0.08% |

10. Example 1.0 g of crude Latanoprostene bunod is dissolved in dichloromethane. Hexane:ethanol mixture is added and the solution is purified by gravity chromatography on a column packed with 100 g of 63-200 micron particle size, 60 Angström pore diameter irregular silica gel, using hexane:ethanol=8:1 mixture eluent. The fractions of appropriate purity are united and evaporated. Yield: 0.52 g (52%).

| Impurities (HPLC area %) | Crude product | Purification chromatography |
| --- | --- | --- |
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.12% |
| Latanoprostene bunod | 72.88% | 98.99% |
| 5,6-trans-Latanoprostene bunod | 2.03% | 0.66% |
| RRT = 1.46 | 1.24% | 0.12% |
| other impurities, total | 0.34% | 0.11% |

11. Example 1.0 of crude Latanoprostene bunod is dissolved in dichloromethane. Hexane:ethanol mixture is added and the solution is purified by gravity chromatography on a column packed with 100 g of 75 micron particle size, 60 Angström pore diameter YMC spherical silica gel, using hexane:ethanol=6:1 mixture eluent. The fractions of appropriate purity are united and evaporated. Yield: 0.57 g (57%).

| Impurities (HPLC area %) | Crude product | Purification chromatography |
| --- | --- | --- |
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.12% |
| Latanoprostene bunod | 72.88% | 99.30% |
| 5,6-trans-Latanoprostene bunod | 2.03% | 0.33% |
| RRT = 1.46 | 1.24% | 0.25% |
| other impurities, total | 0.34% | 0.00% |

12. Example 1.0 g of crude Latanoprostene bunod is dissolved in dichloromethane. Hexane:ethanol mixture is added and the solution is purified by gravity chromatography on a column packed with 25 g of 63-200 micron particle size, 60 Angström pore diameter irregular silica gel, using hexane:ethanol gradient mixtures as eluent. The fractions of appropriate purity are united and evaporated. Yield: 0.64 g (64%).

| Impurities (HPLC area %) | Crude product | Purification chromatography |
| --- | --- | --- |
| RRT = 0.33 | 23.31% | 1.12% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.17% |
| Latanoprostene bunod | 72.88% | 95.45% |
| 5,6-trans-Latanoprostene bunod | 2.03% | 2.80% |
| RRT = 1.46 | 1.24% | 0.36% |
| other impurities, total | 0.34% | 0.10% |

13. Example 1.0 g of crude Latanoprostene bunod is dissolved in dichloromethane. Hexane:ethanol mixture is added and the solution is purified by gravity chromatography on a column packed with 50 g of 63-200 micron particle size, 60 Angström pore diameter irregular silica gel, using hexane:ethanol gradient mixture eluent. The fractions of appropriate purity are united and evaporated. Yield: 0.75 g (75%).

| Impurities (HPLC area %) | Crude product | Purification chromatography |
|---|---|---|
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.17% |
| Latanoprostene bunod | 72.88% | 96.67% |
| 5,6-trans-Latanoprostene bunod | 2.03% | 2.87% |
| RRT = 1.46 | 1.24% | 0.21% |
| other impurities, total | 0.34% | 0.08% |

14. Example 1.0 of crude Latanoprostene bunod is dissolved in dichloromethane. Hexane:ethanol mixture is added and the solution is purified by gravity chromatography on a column packed with 100 g of 63-200 micron particle size, 60 Angström pore diameter irregular silica gel, using hexane:ethanol gradient mixtures as eluent. The fractions of appropriate purity are united and evaporated. Yield: 0.92 g (92%).

| Impurities (HPLC area %) | Crude product | Purification chromatography |
|---|---|---|
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.16% |
| Latanoprostene bunod | 72.88% | 96.88% |
| 5,6-trans-Latanoprostene bunod | 2.03% | 2.80% |
| RRT = 1.46 | 1.24% | 0.08% |
| other impurities, total | 0.34% | 0.08% |

15. Example 1.0 g of crude Latanoprostene bunod is dissolved in dichloromethane. Hexane:ethanol mixture is added and the solution is purified by gravity chromatography on column packed with 100 g of 63-200 micron particle size 60 Angström pore diameter irregular silica gel, using hexane:ethanol gradient mixtures as eluent. The fractions of appropriate purity are united and evaporated. Yield: 0.83 g (83%).

| Impurities (HPLC area %) | Crude product | Purification chromatography |
|---|---|---|
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.17% |
| Latanoprostene bunod | 72.88% | 97.23% |
| 5,6-trans-Latanoprostene bunod | 2.03% | 2.53% |
| RRT = 1.46 | 1.24% | 0.00% |
| other impurities, total | 0.34% | 0.07% |

16. Example 1.0 g of crude Latanoprostene bunod is dissolved in dichloromethane. Hexane:ethanol mixture is added and the solution is purified by gravity chromatography on column packed with 100 g of 75 micron particle size, 60 Angström pore diameter YMC spherical silica gel, using hexane:ethanol=6:1 mixture eluent. The fractions of appropriate purity are united and evaporated. Yield: 0.48 g (48%).

| Impurities (HPLC area %) | Crude product | Purification chromatography |
|---|---|---|
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.12% |
| Latanoprostene bunod | 72.88% | 99.34% |
| 5,6-trans-Latanoprostene bunod | 2.03% | 0.47% |
| RRT = 1.46 | 1.24% | 0.06% |
| other impurities, total | 0.34% | 0.01% |

17. Example 1.0 g of crude Latanoprostene bunod is dissolved in dichloromethane. The solution is purified by gravity chromatography on a column packed with 10 g of 63-200 micron particle size, 60 Angström pore diameter irregular silica gel, using dichloromethane:ethyl acetate gradient mixtures as eluent. The fractions of appropriate purity are united and evaporated. Yield: 0.75 g (75%).

| Impurities (HPLC area %) | Crude product | Purification chromatography |
|---|---|---|
| RRT = 0.33 | 23.31% | 0.00% |
| RRT = 0.70 (Latanoprost) | 0.09% | 0.00% |
| RRT = 0.81 (Latanoprost acid) | 0.00% | 0.00% |
| 15S-Latanoprostene bunod | 0.11% | 0.17% |
| Latanoprostene bunod | 72.88% | 96.36% |
| 5,6-trans-Latanoprostene bunod | 2.03% | 2.73% |
| RRT = 1.46 | 1.24% | 0.65% |
| other impurities, total | 0.34% | 0.09% |

The HPLC procedure used in all above Examples is a stability indicating isocratic normal-phase HPLC assay method which also quantitates the related substances of Latanoprostene bunod in the drug substance. Measurement conditions are the followings:

Assay (HPLC)

Instruments

Instrument: Isocratic HPLC system equipped with UV or diode array detector, electronic data management system and autosampler.

Column: Kromasil 60 5SIL; 250×4.6 mm, 5 μm or equivalent

Chromatographic Conditions

| Eluent: | n-hexane:ethanol:isopropanol:acetic acid = 930:35:35:1 |
| Detection: | 210 nm |
| Flow rate: | 2 ml/min |
| Injected amount | 10 μl |
| Column temperature | 35° C. |
| Run time: | 25 min |

The invention claimed is:

1. Process for the preparation of Latanoprostene bunod of formula (I)

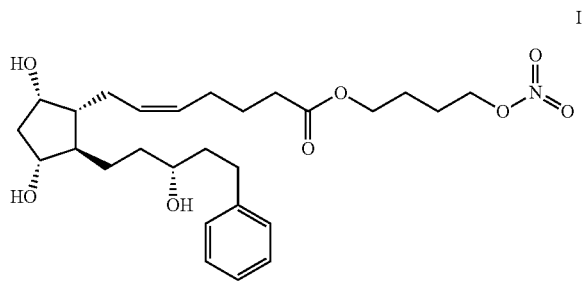 [SMILES: O=C(CCC/C=C\C[C@@H]1[C@@H](CC[C@@H](O)CCc2ccccc2)[C@H](O)C[C@@H]1O)OCCCCO[N+](=O)[O-]]

which meets the following quality requirements:

| Latanoprostene Bunod | |
|---|---|
| Related impurities (HPLC) | |
| 15S-Latanoprostene bunod | ≤0.50% |
| 5,6-trans-Latanoprostene bunod | ≤3.5% |
| Latanoprost | ≤0.50% |
| Latanoprost acid | ≤0.50% |
| Non-identified impurities individually | ≤0.10% |
| Non-identified impurities, total | ≤0.30% |
| Sum of impurities | ≤5.0% | said method consisting of:
purifying the crude Latanoprostene bunod of formula (I) by chromatography, applying normal phase gravity silica gel column chromatography,
using as silica gel
a.) normal phase, irregular silica gel of particle size 63-200 micron, or
b.) normal phase spherical silica gel of particle size 50-150 micron, and
as eluent, an eluent mixture consisting of an apolar and a polar solvent,
and if desired, removing impurities arising from the eluents used for purification chromatography of compound of formula (I) by silica gel filtration chromatography.

2. Process a.) or b.) as defined in claim 1, characterized in that, the eluent mixture contains as apolar solvent straight- or branched-chain aliphatic, cyclic or aromatic hydrocarbons, halogenated aliphatic hydrocarbons or ether-type solvents.

3. Process as defined in claim 2, characterized in that, as apolar solvent pentane, hexane, heptane, cyclohexane, dichloromethane or diisopropyl ether is applied.

4. Process a.) or b.) as defined in claim 1, characterized in that, as polar solvent an alcohol-, ester- or ketone-type solvent containing straight- or branched-chain alkyl group is applied.

5. Process as defined in claim 4, characterized in that, as polar solvent a C1-5 alcohol is applied.

6. Process as defined in claim 3, characterized in that, the eluent mixture is a gradient mixture containing hexane and ethyl alcohol in 6:1-8:1 volume ratios.

7. Process as defined in claim 4, characterized in that, as polar solvent a ketone-type solvent is applied.

8. Process as defined in claim 3, characterized in that, the eluent mixture contains hexane and acetone in 2:1 volume ratio.

9. Process as defined in claim 1, wherein the crude Latanoprostene bunod of formula (I) is purified by filtration chromatography.

10. Process as defined in claim 9, characterized in that, the eluent mixture contains as apolar solvent an optionally halogen-substituted straight or branched open-chain, or cyclic or aromatic hydrocarbon.

11. Process as defined in claim 9, characterized in that, the eluent mixture contains as polar solvent an alcohol-, ether-, ester- or ketone-type solvent containing straight or branched open-chain or cyclic alkyl or cycloalkyl group.

12. Process as defined in claim 11, characterized in that, the eluent mixture contains dichloromethane and ethyl acetate in 2:1 volume ratio.

13. Process as defined in claim 8, characterized in that, the silica gel is normal phase spherical silica gel of particle size 50-150 microns and the prepared Latanoprostene bunod of formula (I) meets the following quality requirements:

| Latanoprostene bunod | |
|---|---|
| Related impurities (HPLC) | |
| 15S-Latanoprostene bunod | ≤0.15% |
| 5,6-trans-Latanoprostene bunod | ≤0.50% |
| Latanoprost | ≤0.10% |
| Latanoprost acid | ≤0.10% |
| Non-identified impurities individually | ≤0.10% |
| Non-identified impurities, total | ≤0.30% |
| Sum of impurities | ≤0.80%. |

14. Process as defined in claim 5, characterized in that, the eluent mixture is a gradient mixture containing hexane and ethyl alcohol in 6:1-8:1 volume ratios.

15. Process as defined in claim 7, characterized in that, the eluent mixture contains hexane and acetone in 2:1 volume ratio.

16. Process as defined in claim 12, characterized in that, the eluent mixture contains dichloromethane and ethyl acetate in 2:1 volume ratio.

17. Process as defined in claim 2, characterized in that, as the apolar solvent, hexane is applied.

18. Process as defined in claim 4, characterized in that, as the polar solvent, ethyl alcohol or isopropyl alcohol is applied.

19. Process as defined in claim 4, characterized in that, as the polar solvent, acetone is applied.

* * * * *